(12) United States Patent
Hartwig et al.

(10) Patent No.: US 9,050,256 B2
(45) Date of Patent: Jun. 9, 2015

(54) ORAL DOSAGE FORM, COMPRISING AT LEAST ONE BIOLOGICALLY ACTIVE AGENT, FORMULATION AUXILIARY SUBSTANCES AND MAGNETIZABLE PARTICLES

(75) Inventors: Benedikt Hartwig, Darmstadt (DE);
Norbert Windhab, Hofheim (DE);
Melanie Liefke, Ober-Ramstadt (DE);
Juan Tome Alcalde, Madrid (ES);
Michael Damm, Roedermark (DE);
Rosario Lizio, Dieburg (DE); Michael Gottschalk, Ober-Ramstadt (DE);
Angela Olf, Gross-Rohrheim (DE);
Christian Meier, Darmstadt (DE);
Andreas Gryczke, Riedstadt (DE)

(73) Assignee: Evonik Röhm Gmbh, Darmstadt (DE)

( * ) Notice: Subject to any disclaimer, the term of this patent is extended or adjusted under 35 U.S.C. 154(b) by 787 days.

(21) Appl. No.: 13/390,353

(22) PCT Filed: Aug. 30, 2010

(86) PCT No.: PCT/EP2010/062641
§ 371 (c)(1),
(2), (4) Date: Feb. 14, 2012

(87) PCT Pub. No.: WO2011/026808
PCT Pub. Date: Mar. 10, 2011

(65) Prior Publication Data
US 2012/0143039 A1 Jun. 7, 2012

Related U.S. Application Data

(60) Provisional application No. 61/239,613, filed on Sep. 3, 2009.

(30) Foreign Application Priority Data

Sep. 3, 2009 (DE) .......................... 10 2009 029 170

(51) Int. Cl.
| | |
|---|---|
| *A61B 5/055* | (2006.01) |
| *A61K 9/20* | (2006.01) |
| *A61K 9/28* | (2006.01) |
| *A61K 9/48* | (2006.01) |
| *A61K 9/50* | (2006.01) |
| *A61K 9/00* | (2006.01) |

(52) U.S. Cl.
CPC ............. *A61K 9/2072* (2013.01); *A61K 9/0053* (2013.01); *A61K 9/0009* (2013.01); *A61K 9/2095* (2013.01); *A61K 9/2813* (2013.01); *A61K 9/2846* (2013.01); *A61K 9/2866* (2013.01); *A61K 9/4808* (2013.01); *A61K 9/4816* (2013.01); *A61K 9/4833* (2013.01); *A61K 9/4883* (2013.01); *A61K 9/5094* (2013.01)

(58) Field of Classification Search
None
See application file for complete search history.

(56) References Cited

U.S. PATENT DOCUMENTS

| 5,079,006 A | 1/1992 | Urquhart |
|---|---|---|
| 2005/0163866 A1 | 7/2005 | Alex et al. |

FOREIGN PATENT DOCUMENTS

| CN | 1094577 A | 11/1994 |
|---|---|---|
| CN | 1785430 A | 6/2006 |
| CN | 1909869 A | 2/2007 |
| DE | 39 40 260 A1 | 9/1990 |
| DE | 10 2008 033 662 | 1/2010 |
| DE | 10 2008 033 662 A1 | 1/2010 |
| EP | 0 303 045 | 2/1989 |
| EP | 0 317 893 A2 | 5/1989 |
| EP | 1 557 151 | 7/2005 |
| JP | 2004-331750 A | 11/2004 |
| JP | 2007-518501 A | 7/2007 |
| WO | WO 2004/096188 A1 | 11/2004 |
| WO | WO 2008/009589 A2 | 1/2008 |

OTHER PUBLICATIONS

Search Report issued Sep. 24, 2010 in German Patent Application No. 10 2009 029 170.9 (with English language translation).
Office Action issued Sep. 1, 2014 in Japanese Patent Application No. 2012-527293 (with English language translation).
Werner Weitschies, et al., "High-Resolution Monitoring of the Gastrointestinal Transit of a Magnetically Marked Capsule" Journal of Pharmaceutical Sciences, vol. 86, No. 11, 1997, pp. 1218-1222.

(Continued)

*Primary Examiner* — Michael G Hartley
*Assistant Examiner* — Melissa Perreira
(74) *Attorney, Agent, or Firm* — Oblon, McClelland, Maier & Neustadt, L.L.P.

(57) ABSTRACT

The invention relates to an oral dosage form, comprising at least one biologically active agent, formulation auxiliary substances and magnetizable particles, wherein the dosage form has an at least two phase composition, wherein the phases can dissolve in the body after oral administration due to their formulation and the magnetizable particles are bound in formulation auxiliary substances and are present in a magnetized state, wherein the magnetized particles are present in at least two phases of the dosage form and generate magnetic fields, wherein these phases dissolve at different times in the body after oral administration, and wherein the magnetic field strength with respect to time, position and movement in the body is acquired using a detection system and can be evaluated using a computer-based evaluation system.

20 Claims, 4 Drawing Sheets

(56) References Cited

OTHER PUBLICATIONS

Figure 1:
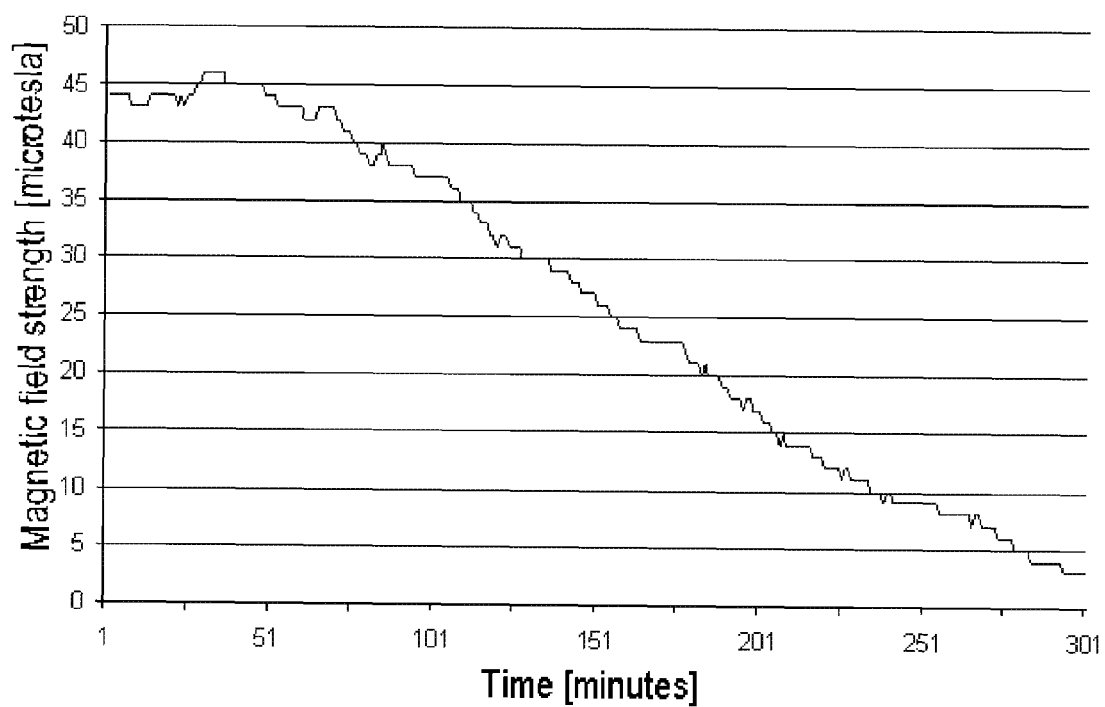

Combined Chinese Office Action and Search Report issued Oct. 21, 2013 in Patent Application No. 201080039021.4 (with English language translation).

Weitschies, W., et al., "Bioavailability of amoxicillin and clavulanic acid from extended release tablets depends on intragastric tablet deposition and gastric emptying," European Journal of Pharmaceutics and Biopharmaceutics, vol. 70, No. 2, pp. 641-648 (Oct. 1, 2008).

Weitschies, W., et al., "Magnetic Marker Monitoring: High resolution real-time tracking of oral solid dosage forms in the gastrointestinal tract," European Journal of Pharmaceutics and Biopharmaceutics, vol. 74, No. 1, pp. 93-101, (Jan. 1, 2010).

Weitschies, W., et al., "Magnetic Marker Monitoring: An application of biomagnetic measurement instrumentation and principles for the determination of the gatrointestinal behavior of magnetically marked solid dosage forms," Advanced Drug Delivery Reviews, vol. 57, No. 8, pp. 1210-1222, (Jun. 15, 2005).

International Search Report Issued Nov. 18, 2011 in PCT/EP10/62641 Filed Aug. 30, 2010.

ORAL DOSAGE FORM, COMPRISING AT LEAST ONE BIOLOGICALLY ACTIVE AGENT, FORMULATION AUXILIARY SUBSTANCES AND MAGNETIZABLE PARTICLES

FIELD OF THE INVENTION

The invention relates to the field of monitoring oral dosage forms in respect of their intake into the body and their dissolution in the body using magnetic fields integrated into the dosage forms.

PRIOR ART

WO 98/07364 describes a monitoring system for monitoring the regular intake of a medicine or dosage form. A detection instrument for non-invasive detection of a substance, contained in the dosage form in the body of the patient, is included as a system component. The detection instrument in this case is designed for reagent-free, direct measurement of a physically measureable parameter correlated to the presence of the substance in the body of the patient. In particular, a marker substance is used which measurably influences electromagnetic radiation radiated into the body. The electromagnetic radiation is preferably light, particularly in the visible or infrared band. The monitoring system permits the detection of the intake of the dosage form in the body and systemic following of the marker in the bloodstream. By way of example, the detection instrument can comprise a sensor similar to a watch.

Weitschies et al. (2005), *Advanced Drug Delivery Reviews* 57, 1210-1222, describe so-called "magnetic marker monitoring". Here, a magnetic field is integrated into an oral dosage form, e.g. a capsule or a tablet, which magnetic field can be measured after oral intake of the dosage form by means of a detection device. By way of example, magnetite particles ($Fe_3O_4$) enclosed in a pharmaceutical binder are suitable for generating a magnetic field. By way of example, tablets can be coated with gastric juice resistant polymers which contain magnetite particles, for example EUDRAGIT® L. Using a so-called SQUID device, the presence of the magnetically marked tablet can be detected directly after its intake into the body. Once the gastric juice resistant polymer coating dissolves in the region of the intestine, the magnetic signal is lost. Further differentiation is not possible.

Figure 3:
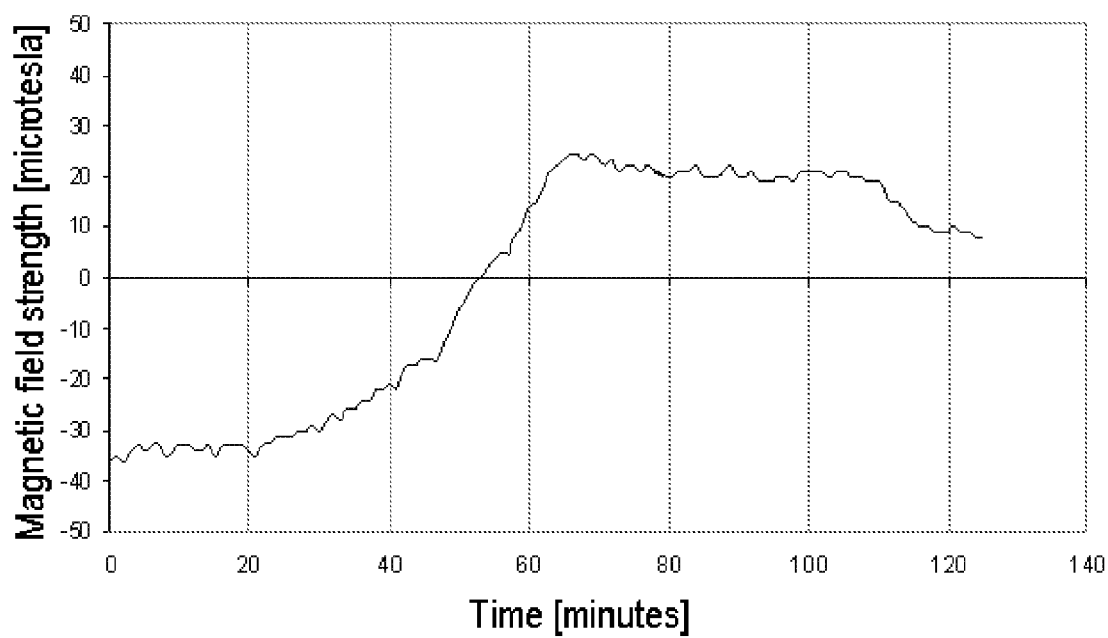

Weitschies et al. (2010) *European Journal of Pharmaceutics and Biopharmaceutics* 74, p. 93-101, describes high resolution real-time tracking of oral solid dosage forms in the gastro intestinal tract by magnetic marker monitoring. A magnetically labelled dual layer tablet with an immediate release layer and an extended release layer is shown in one of the figures. Both layers are magnetically labeled by drilling small bore holes in the layers where the bore holes are filled with iron oxide powder. The bore holes are sealed with butyl cyanoacrylate or Mg-stearate. The tablets were magnetized for 5 minutes in a homogeneous magnetic field (Weitschies et al. (2008) *European Journal of Pharmaceutics and Biopharmaceutics* 70, p. 641-648, s. *Materials and methods*, 2.1 *Magnetic labelling of tablets*, cited in Weitschies et al. (2010) in FIG. 3 as [42]). Thus the magnetic fields incorporated in the two layers are orientated in the same direction or orientation and thus have the same alignment.

This is becomes since the relative magnetic moment shown in another figure seems to decrease only. Furthermore the relative magnetic moments measured in a healthy volunteer under fastening conditions, at the beginning of a meal and 30 min after a meal differ remarkably so that no kind of signature which would be typical for the oral dosage form used can detected. The problem of magnetic labeling of oral dosage forms in order to produce a typical signature which unambiguously allows the identification of the oral dosage forms after ingestion is not mentioned.

DE 102008033662A1 describes a pharmaceutical dosage form which is a capsule or a tablet and which includes at least two active magnetic pieces. The at least two active magnetic pieces are positioned in an unstable position to each other and are biocompatible. Typical examples for magnetic pieces are permanent magnets or magnetized materials like iron. To position the magnetic pieces in the unstable position it is suggested to use special coatings or stabilizing inter-pieces. Biocompatibility shall be established by coating the magnetic pieces with biocompatible coating materials. After dissolution of the pharmaceutical form the active magnetic pieces are set free and shall position themselves to a stable position by magnetic attraction in the form of aggregates pieces. This change in the magnetic field shall be detectable from outside the human body. Then the aggregated magnetic peaces shall leave the body via the intestine.

In contrast to the present invention the magnetic fields of DE 102008033662A1 do not dissolve. The magnetic pieces remain as they are and even increase their size by aggregating due to magnetic attraction. Even if the magnetic pieces might be made biocompatible by coating, it cannot be excluded that they may cause irritations or even might cause injures by mechanical stress on the inner surfaces of the intestine when passing through the intestine in the form aggregated pieces. Furthermore it becomes apparent that the positioning of the active magnetic pieces in an unstable position within a pharmaceutical dosage form, which is a capsule or a tablet, might be quite difficult to perform. The need to provide biocompatible coating on the magnetic pieces is another disadvantage of the pharmaceutical dosage form according to DE 102008033662A1.

LIST OF FIGURES AND REFERENCE SIGNS

Figure 2:
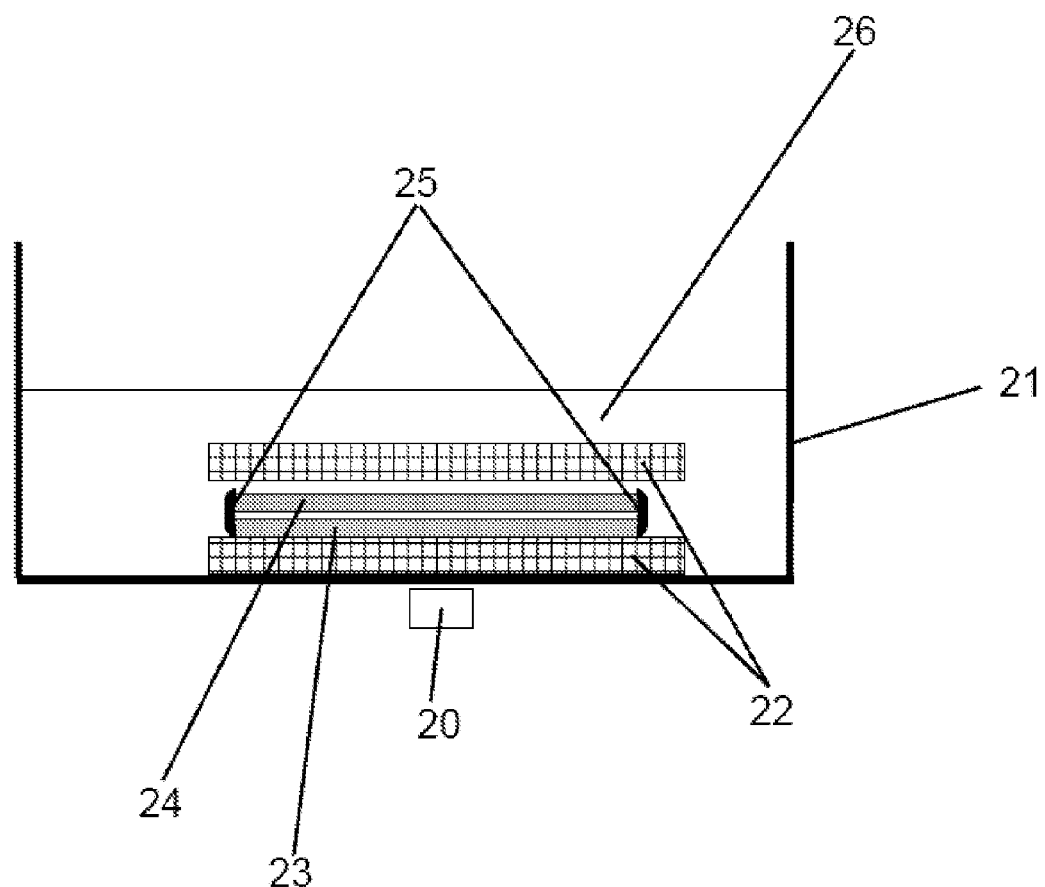
Figure 4:
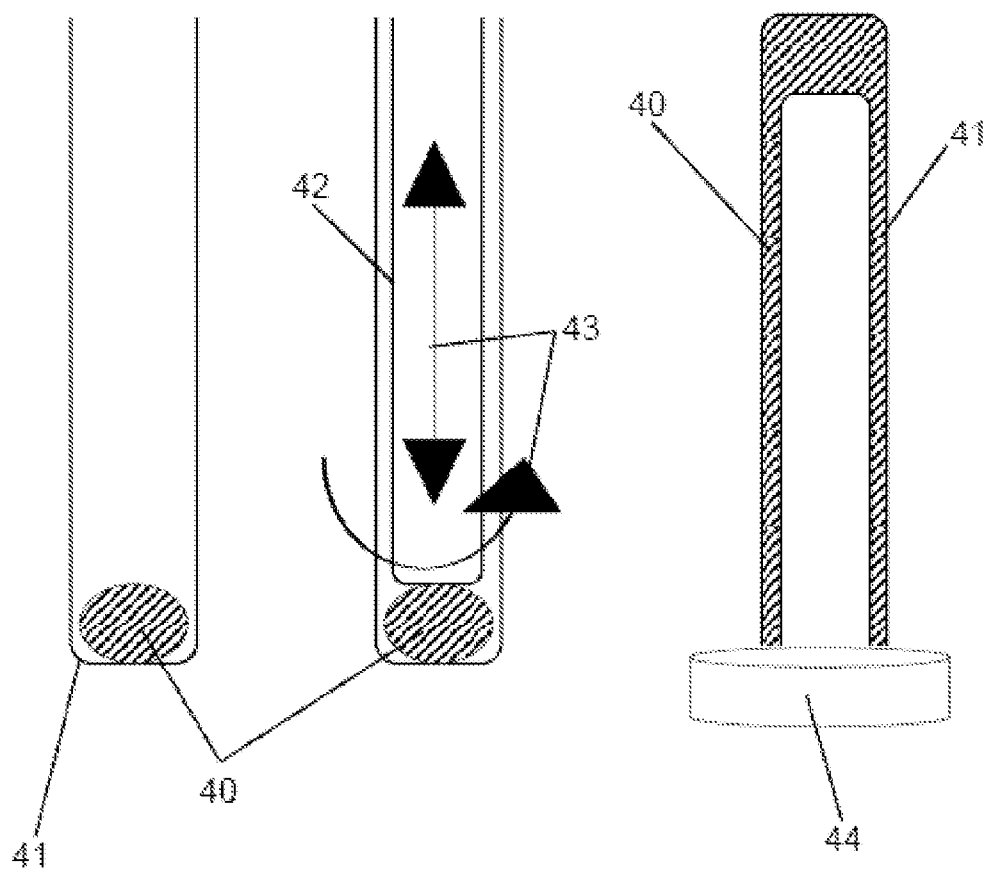

The invention is explained by the following figures:
FIG. 1: Magnetic field diagram for example 1
FIG. 2: Trial arrangement for example 3
20 Hall sensor, connected to measuring instrument
21 Petri dish
22 Plastic grid
23 EUDRAGIT® E PO/iron oxide film
24 EUDRAGIT® FS30/iron oxide film
25 Plastic clamps
26 Liquid medium (distilled $H_2O$, 0.1 HCl or 0.1 NaOH)
FIG. 3: Magnetic field diagram for example 3
FIG. 4: Explanation of the production of the magnetized inner coating for half of a hard gelatin capsule
  40 Paste, comprising iron oxide powder
  41 Hard gelatin capsule, size 0, bottom half
  42 Hard gelatin capsule, size 1, bottom half
  43 Movement vectors of the inner capsule for distributing the EUDRAGIT®/PEG/iron oxide mixture
  44 Permanent magnet

PROBLEM AND SOLUTION

Inadvertently or deliberately not following intake prescriptions for medicines constitutes an economic problem since this often results in illnesses not being able to be treated as efficiently as would be possible if the medicine was taken in correctly. This creates undesired additional expenditure in the health service. Furthermore, not following intake prescriptions can lead to the patient putting him/herself at risk, particularly in the case of critical medicines such as cardiovascular remedies. Hence there is a need for detection systems for monitoring the actual intake of the medicine both in general and in particular when prescribing medicaments critical to the acute state of health.

Clinical studies often have the problem that the dosage forms provided for intake are accidentally or even deliberately not taken by patients at the prescribed intervals by a certain non-negligible percentage. If this is not noticed, the results of such clinical studies cannot be evaluated on the basis of reliable data.

The monitoring system described in WO 98/07364 for monitoring the regular intake of a medicine or a dosage form is only suitable if corresponding marker substances are available in the dosage form itself. This significantly restricts the possible fields of application. Additionally, a large amount of electromagnetic radiation energy is required for the purposes of detection and so undesired side-effects such as strong heating of the irradiated body parts cannot be excluded. The "magnetic marker monitoring" described in the prior art opens up a further possibility for monitoring. However, the complexity required for detecting the intake of a dosage form has been extremely high until now. The SQUID apparatuses used by Weitschies et al. (2005) are expensive and practically immovable.

Weitschies et al. (2010) *European Journal of Pharmaceutics and Biopharmaceutics* 74, p. 93-101, describes a magnetically labelled dual layer tablet with an immediate release layer and an extended release layer is show in one of the figures. Both layers are magnetically labeled by drilling small bore holes in the layers where the bore holes are filled with iron oxide powder. The bore holes are sealed with butyl cyanoacrylate or Mg-stearate. The tablets were magnetized for 5 minutes in a homogeneous magnetic field (Weitschies et al. (2008) *European Journal of Pharmaceutics and Biopharmaceutics* 70, p. 641-648, s. *Materials and methods*, 2.1 *Magnetic labelling of tablets*, cited in Weitschies et al. (2010) in FIG. 3 as [42]). Thus the magnetic fields incorporated in the two layers are orientated in the same direction or orientation and thus have the same alignment. The dual layer tablet according to the Weitschies et al. (2010) publication has two major disadvantages. Since bore holes are filled with iron oxide powder the magnetizable particles only attached to are no integrative part but of the phases which different dissolution behaviour. This means when one of these phases starts to dissolve the bore hole cavities may be become open sooner or later in a not controlled way. Thus magnetic moment resulting from the integrated magnetic fields will vary after ingestion in a not controlled manner even if the conditions in the human body were taken as constant. Since they are not there is additional variation. Therefore this oral dosage form does not form a suitable basis for an oral dosage form which may provide a detectable unequivocal magnetic signature profile. Furthermore since the magnetic fields incorporated in the two layers are orientated in the same direction or orientation and thus have the same alignment, it is not possible to detect an unequivocal magnetic signature profile, since there is no clear differentiation between the dissolution of the two phase over the time.

DE 102008033662A1 describes a pharmaceutical form which is a capsule or a tablet and which includes at least two active magnetic pieces. The at least two active magnetic pieces are positioned in an unstable position to each other and biocompatible. Typical examples for magnetic pieces are permanent magnets or magnetisable materials like iron. After dissolution of the pharmaceutical form the active magnetic pieces position themselves to a stable position by magnetic attraction, whereby the detectable magnetic field adepts a change. As shown in the figures the magnetic parts inside the pharmaceutical form are aligned in the same direction. Since the magnetic parts are not bound like the magnetizable particles of the present invention in formulation auxiliary substances, these parts will be set free in a not controlled way. Thus it is not possible to detect an unequivocal magnetic signature profile.

The problem was considered to be that of providing an oral dosage form comprising at least one biologically active agent, formulation auxiliary substances and magnetically orientable particles which can be used advantageously in clinical studies. In particular, deviations from the intake intervals and manipulations of the system should be reliably detectable. Furthermore, a reliable and individual detection of the dosage form should be possible.

The object is achieved by:

an oral dosage form, comprising at least one biologically active agent, formulation auxiliary substances and magnetizable particles, wherein the dosage form has an at least two phase composition, wherein the phases dissolve in the body after oral administration due to their formulation and the magnetizable particles are bound in formulation auxiliary substances and are present in a magnetized state, wherein the magnetized particles are present in at least two phases, preferably in three or four or five phases of the dosage form and generate magnetic fields, wherein two or at least two of the magnetic fields have different alignments, wherein these phases dissolve at different times in the body after oral administration, whereby the magnetic fields extinguish after dissolution of the phases, and wherein the magnetic field strength with respect to time, position and movement in the body is acquired using a detection system and can be evaluated using a computer-based evaluation system.

The dosage form according to the invention differs from the prior art particularly in that at least two magnetic fields are integrated in different phases, with the phases being able to dissolve in the body after oral intake due to their formulation and where the two or at least two of the magnetic fields have different alignments. This firstly causes a superposition of at least two magnetic fields. Once the first magnetic field has been dissolved, this superposition is lifted completely, or partly, if further magnetic fields are present, until even the last magnetic field is lost after the corresponding phase has dissolved. Because of the different alignments the two or at least two of the magnetic fields an up and down signal is generated as the dosage form dissolves, which signal can be associated with a certain dosage form by its signature.

Hence, after incorporation in the dosage form, the magnetic fields yield an up and down intensity spectrum over time which is characteristic for the dosage form and which can be acquired using the detection system and the evaluation system. Since the specific at least two-stage signal is only emitted after intake into the body as a result of the dosage form dissolving, undiscovered manipulation of the system is hardly possible any more. The signature-like signal can be used not only in clinical studies but also for protection against product piracy if the inventive dosage form is also provided with a corresponding magnetic marker in the subsequent sales form.

Embodiment of the Invention

The oral dosage form according to the invention comprises at least one biologically active agent, formulation auxiliary substances and magnetizable particles.

Magnetizable Particles

Within the meaning of the invention, magnetizable particles are particles, preferably particles composed of a ferromagnetic material, which can be magnetized by means of a magnetic field acting from the outside, either or both as a result of the orientation of said particles and/or by magnetizing the elementary magnetic particles in their interior, and therefore, in total, said particles form a magnetic field. Prior to magnetization, the particles are in a magnetically unordered state in respect of their orientation and the alignment of the elementary magnetic particles in their interior and so practically no magnetic field which would exceed the surrounding noise signal (< or <<1 µT) can be measured by a teslameter. A combination or superposition of both effects, of both the orientation of the particles and the magnetization of the elementary magnetic particles in the interior of the particles, can be assumed in many cases and is preferable. The magnetizable particles are preferably embedded in a matrix of formulation auxiliaries. The matrix is used for fixing the magnetic field and for monitoring the release of the agent from the dosage form.

As a result of the influence of the magnetic field acting from the outside, the magnetizable particles can, provided they are in a matrix, a solid or frozen matrix, which does not permit their movement be magnetized by the alignment of the elementary magnetic particles in their interior. This results in a magnetic field that continues to exist even when the magnetic field acting from the outside has been removed.

As a result of the influence of the magnetic field acting from the outside, the magnetizable particles can, provided they are in a matrix, preferably a matrix in a liquid, gel or melt state, which permits their movement, be oriented in their alignment by the magnetic field acting from the outside, primarily along the magnetic field lines. By way of example, a dispersion or suspension, which comprises magnetizable particles, is based on a film-forming polymer used to generate a spray coating and in the drying state transitions into a colloidal or gel-like state on the dosage form, can be magnetized in this state. This alignment already generates a magnetic field. If this orientation is fixed, for example by the transition of the matrix into a solid state, this results in a magnetic field that continues to exist once the magnetic field acting from the outside has been removed. A superposition of the two effects, both the orientation of the particles and by orientating the elementary magnetic particles in the interior of the particles, can be assumed. The magnetizable particles are preferably magnetite ($Fe_3O_4$) or maghemite ($Fe_2O_3$). Magnetite and maghemite can be considered to be safe toxicologically and pharmacologically and are used, inter alia, as nontoxic insoluble pigments in foodstuffs or medicaments. The possible toxicity of other magnetizable particles, e.g. complex doped inorganic compositions (e.g. NdFeB) known to a person skilled in the art, can also be reduced by specific formulations in the dosage form, e.g. by vitrification in silicates. If need be, other magnetically orientable particles such as the ferrites $MnFe_2O_4$ or $MgFe_2O_4$ can also be suitable. For the purposes of reliable detection, there should be no less than approximately 0.01 mg of magnetizable particles per magnetic field or in total in a dosage form, e.g. in a tablet. In extreme cases, the highest possible content can reach the order of 1 g or below 10 g. Expediently, each magnetic field can comprise 0.05 to 100, preferably 0.1 to 50, in particular 0.2 to 20 mg of magnetizable particles. The average particle size of the magnetizable particles can for example lie in the range from 1 nm to 1 mm, preferably from 100 nm to 100 µm.

After dissolution of the phase of the oral dosage form respectively the matrix that originally contained the magnetizable particles embedded in formulation auxiliaries, the magnetic field disappears or extinguishes and the magnetizable particles are set free in the intestine. Due to their comparably small size and individually rather low magnetic properties, they will get freely distributed within the intestine and will not get aggregated. Thus there should not be any problems or irritations in connection with the magnetizable particles at the surface of the intestine. Disappearance or extinguish of the magnetic field after dissolution of the corresponding phase of the oral dosage form shall mean that there is practically no magnetic field left which would exceed the surrounding noise signal (< or <<1 µT).

Magnetic Fields

Magnetic fields within the meaning of the invention are magnetic fields which set themselves apart from the surrounding noise signal, in particular magnetic fields with a strength of the order of at least 1, preferably at least 10 µT, measured by a teslameter at a distance of 1, preferably 2 cm.

The orientation of the magnetically orientable or magnetizable particles can be generated by applying an external magnetic field. By way of example, permanent magnets, electromagnets and shiftable and spatially structurable magnetic fields are suitable for generating the external magnetic fields. The external magnetic field to be applied can expediently have a magnetic flux density in the range of for example 0.01 to 0.9, in particular of 0.1 to 0.8 T. The external magnetic field can expediently be applied at a distance of 0.1 to 2 cm. The magnetic fields comprised in the dosage form can have the same or different alignments.

However two or at least two of the magnetic fields preferably have different or opposite alignments. Different or opposite alignment of two magnetic fields shall mean that the magnetic fields are more or less orientated in the opposite direction and thus the overall resulting magnetic field strength which can be measured is the difference of the vectors of both magnetic field strengths. Different or opposite direction shall mean every orientation where the sum of the two magnetic field strengths is less than the magnetic field strength of the stronger one of both. Preferably different or opposite direction shall mean an orientation where the sum of the vectors the two magnetic field strengths is less than 50, less than 60, less than 70, less than 80, less than 90 or 100% of the sum of the two magnetic fields. For instance, in the case of two magnetic fields of identical intensity and perfectly orientation in the opposite direction the sum of these two magnetic fields is zero. This is by 100% less of the sum of the two magnetic field strengths because the vectors of the magnetic fields or magnetic fields strengths respectively add up to zero or extinguish each other respectively.

The advantage of the presence of two or at least two magnetic fields with different alignments is that after the dissolution of one of the magnetic fields, the detection system will detect the resulting magnetic field or respectively a change in the direction of the overall magnetic field. This results in a more sensitive and clearer detection of the magnetic signature of the oral dosage form.

If the two or all of the magnetic fields had the same alignments the detection system could in the course of the dissolution of the oral dosage form only detect the diminishing of an overall magnetic field in one direction, which gives more room for artificial effects and interpretation problems which could influence the accuracy of the signature detection and of the signature system itself.

The strength of the magnetic fields, measured with a teslameter at a distance of 1 cm, can lie in the range of for example 1 to 1000, preferably 2 to 500, particularly preferably 5 to 250 µT. A distance of 5-20 cm from the skin surface has to be assumed when measuring the magnetic fields within the human body. Appropriate detection systems or sensors must still be able to detect the magnetic fields, the intensity of which is markedly reduced as a result of the distance. Sensors which are based on Hall sensors can be used for this purpose.

Characteristic Intensity Profile

After incorporation into the dosage form, the magnetic fields or the superposition thereof result in a characteristic intensity profile over time for the dosage form, which profile can be acquired using the detection system and the evaluation system.

Alignments

The following table shall explain possible alignments of the magnetized phases of different oral dosage forms without limiting the invention to the inventive examples presented here.

Examples No. 1 to 3 explain oral dosage forms with two magnetized phases which dissolve one after another at different times in the body after oral administration. Examples No. 4 to 9 explain oral dosage forms with three magnetized phases which dissolve one after another at different times in the body after oral administration. In each case of the examples phase 1 dissolves first, then phase 2 and in the case of examples No. 4 to 9 then phase 3.

The arrow up (↑) shall indicate that the magnetizable particles in the certain phase are present in a magnetized state and form a magnetic field in one alignment or direction (north/south for example). The arrow down (↓) shall indicate that the magnetizable particles in the certain phase are present in a magnetized state and form a magnetic field in the opposite direction or in opposite alignment(south/north in this example, 180° angle to north/south) to the magnetic field with the arrow up (↑) indication). The strength of the magnetic field in assumed to have the relative value plus one arrow up (↑) or minus one arrow down (↓).

Directly after ingestion there is no phase dissolved. At this time point all the magnetic field strengths included in the oral dosage form add up to a total sum.

When phase 1 is dissolved the remaining magnetic field strength is the magnetic field strength of phase 2 in the case of examples No. 1 to 3 or the sum of the magnetic field strength of phase 2 and phase 3 in the case of examples No. 4 to 9. When phase 2 is dissolved the remaining magnetic field strength is zero in case of examples No. 1 to 3 or the magnetic field strength of the remaining phase 3 in the case of examples No. 4 to 9.

In the examples 1, 4 and 7 all the phases of the oral dosage form have magnetic fields with the same alignments. In these cases only a descending or only an increasing magnetic moment can be detected over the time. This makes it difficult to identify an unequivocal signature profile for the certain oral dosage form. Therefore these examples are not according to the invention.

In all other examples 2, 3,5 to 6 and 8 and 9, the magnetic moment moves up and down or down and up which makes it much easier to identify an unequivocal signature profile for the certain oral dosage form. Therefore these examples are according to the invention

TABLE 1

| Example No. | Alignment | | | Sum of magnetic field strengths | | | | According to the invention |
|---|---|---|---|---|---|---|---|---|
| | Phase 1 | Phase 2 | Phase 3 | No phase dissolved | Phase 1 dissolved | Phase 2 dissolved | Phase 3 dissolved | |
| 1 | ↑ | ↑ | — | 2 | 1 | 0 | — | No |
| 2 | ↑ | ↓ | — | 0 | −1 | 0 | — | Yes |
| 3 | ↓ | ↑ | — | 0 | 1 | 0 | — | Yes |
| 4 | ↑ | ↑ | ↑ | 3 | 2 | 1 | 0 | No |
| 5 | ↓ | ↑ | ↑ | 1 | 2 | 1 | 0 | Yes |
| 6 | ↓ | ↓ | ↑ | −1 | 0 | 1 | 0 | Yes |
| 7 | ↓ | ↓ | ↓ | −3 | −2 | −1 | 0 | No |
| 8 | ↓ | ↑ | ↓ | −1 | 0 | −1 | 0 | Yes |
| 9 | ↑ | ↓ | ↑ | 1 | 0 | 1 | 0 | Yes |

General Production of Dosage and Medicament Forms

A person skilled in the art in the field of pharmacy and, in particular, galenics knows all pharmaceutical production methods. These can easily be applied by said person having knowledge of the invention so as to produce corresponding magnetically marked dosage forms according to the invention. In particular, a person skilled in the art is very familiar with the production of pellets and cores containing agents, the application of formulation auxiliaries, the production of polymer encapsulations, the production of tablets in general, in particular the production of tablets by pressing, and the production and filling of capsules.

Details can be gathered from established textbooks, e.g.:

Voigt, R. (1984): Lehrbuch der pharmazeutischen Technologie [Textbook of pharmaceutical technology]; Verlag Chemie Weinheim—Beerfield Beach/Florida—Basle.

Sucker, H., Fuchs, P., Speiser, P.: Pharmazeutische Technologie [Pharmaceutical technology], Georg Thieme Verlag Stuttgart (1991), in particular chapters 15 and 16, pp. 626-642.

Gennaro, A., R. (Editor), Remington's Pharmaceutical Sciences, Mack Publishing Co., Easton Pa. (1985), chapter 88, pp. 1567-1573.

List, P. H. (1982): Arzneiformenlehre [Medicaments teachings], Wissenschaftliche Verlagsgesellschaft mbH Stuttgart.

Dosage Form According to the Invention

The oral dosage form according to the invention can be practically any type of oral dosage form as long as it has at least two different phases for integrating magnetic fields and as long as these phases dissolve in the body at different times after oral administration. Hence the dosage form comprises at least two phases. By way of example, it can have two, three, four, five or more phases.

The phases of the dosage form in which the magnetic fields are localized can be, for example, the core, polymer film encapsulations or capsule halves, or combinations of these parts. Hence, the term "phase" can be equivalent to a delimitable part or a separately producible or produced part of the dosage form.

By way of example, the dosage form can have the form of a filled capsule, a filled capsule which is enclosed in a further capsule or an encapsulated tablet.

A first phase of the encapsulated tablet can for example be provided with a gastric juice resistant, intestinal juice soluble film encapsulation which has magnetized particles and thus forms a magnetic field. The core of the tablet can constitute a second phase comprising magnetized particles which only dissolves, e.g. in a delayed fashion, once the gastric juice resistant, intestinal juice soluble film encapsulation has been dissolved and which slowly releases the magnetized particles together with the agent.

The dosage form can for example have a core in the form of a flat tablet comprising the agent, wherein the two flat sides of the tablet are provided with in each case one magnetized film by a fusing procedure. In the process, the magnetized films should be in such a condition that they dissolve in the body at different times or at different locations.

The dosage form may have an at least three phase composition, wherein the magnetized particles are present in three phases of the dosage form.

The dosage form may have an at least three phase composition, wherein one or at least one phase comprises the biologically active agent but no magnetized particles. This has the advantage that the phases comprising magnetized particles but no active ingredient may be produced separately and may be assembled together with a phase containing the biologically active agent but no magnetized particles. This may lead to a simplified production process.

One phase comprising magnetized particles may be formulated as an immediate release phase. This has the advantage that the receiving electronic may detect an early up or down in the magnetic moment which helps to increase the sensitivity for the detection of the magnetic profile.

Method for Producing the Dosage Form According to the Invention

The invention relates to a method for producing a dosage form which comprises at least two phases forming a magnetic field, wherein the individual phases are produced by magnetizable particles being bound by formulation auxiliaries and the magnetizable particles are magnetized by a magnetic field acting from the outside and so magnetic fields develop in the phases, wherein the magnetization of the magnetizable particles can be undertaken before or after joining of the dosage form and the phases can dissolve in the body at different times due to the positioning in the dosage form or due to the formulation auxiliary used in the phase.

Preferably, the phases comprising a magnetic field are produced by binding magnetizable particles with formulation auxiliaries which transition from a nonsolid state to a solid state during the production, wherein the magnetizable particles are oriented with the aid of a magnetic field acting from the outside during the none solid state of the formulation auxiliary and the orientation and magnetization is fixed during the solidification of the formulation auxiliary and so magnetic field comprising phases are formed.

Preferably, the phases forming a magnetic field are produced separately from one another and, possibly with further phases which do not have a magnetic field, are subsequently joined together to form a dosage form according to the invention.

By way of example, a magnetized polymer film can be obtained by producing a preparation comprising a film-forming polymer, a solvent and magnetically orientable particles, pouring said preparation into a thin film in the nonsolid state, and applying a magnetic field to orient the magnetizable particles, as a result of which the magnetizable particles orient themselves in the composition and form a magnetic field which is fixed after solidification.

One or more magnetic fields can for example be introduced by using one or more magnetized capsule halves as phase or phases of the dosage form. This applies to both hard gelatin capsules and soft gelatin capsules, and also to capsules or capsule halves of different materials, e.g. capsules of hydroxypropylmethylcellulose (HPMC).

Magnetized capsule halves be can obtained by producing capsule halves from preparations, comprising a film-forming polymer, a solvent and magnetizable particles, produced using a dip-coating method, a magnetic field being applied to the capsule halves in the nonsolid state, as a result of which the magnetizable particles orient themselves in the composition and form a magnetic field which is fixed after solidification.

Capsule halves can for example be coated on the inside with a formulation auxiliary which comprises magnetically orientable particles (see example 5). Additionally, the formulation auxiliary which is still liquid and comprises magnetically orientable particles can be filled into a finished capsule half. The liquid can be distributed evenly on the inner wall of the capsule, for example by using a stamp which fills out the interior of the capsule half. The magnetically orientable or magnetizable particles can now be oriented by the influence of an external magnetic field while the formulation auxiliary is still in a gel state. The orientation of the particles is fixed after the inner coating has dried. The capsule half obtained in this manner now comprises a phase lying on the inside which forms a magnetic field. The capsule half can subsequently be combined with further phases which likewise form magnetic fields but dissolve at different times or at different locations in the body. The capsule half coated on the inside can for example be combined with a fitting capsule half which has been correspondingly coated on the outside. So as to complete the dosage form, agent-containing pellets, for example, which do not have to have a magnetic field, can be filled into the magnetized capsule halves.

One or more magnetic fields can for example also be introduced by one or more magnetized, extruded cores being used as phase or phases of the dosage form. In this case, these can for example be correspondingly magnetized cores or pellets which contain the agent.

Extruded cores can be produced by means of strand extrusion from preparations of a film-forming thermoplastic polymer, possibly with an agent and magnetizable particles, and by subsequent comminution of the strand into elongate or planar bodies. The extruded strand of the preparation in the melt state can pass a magnetic field applied from the outside, as a result of which the magnetically orientable or magnetizable particles in the composition are oriented and a magnetic field forms therein which is fixed after the cooling of the strand in the elongate or planar bodies.

A phase which comprises magnetically orientable particles can, particularly in the form of encapsulating films, be inserted into or applied to the dosage form by spray application of solutions or dispersions which comprise filmable polymers and the magnetically orientable particles, and can be combined with other phases which comprise magnetically orientable or oriented particles.

Formulation Auxiliary for the Magnetically Orientable or Magnetizable Particles

The magnetically orientable or magnetizable particles are bound or embedded into a matrix with formulation auxiliaries. The formulation auxiliaries can be present in the form of a powder or in a form which transitions from a nonsolid state to a solid state during the production.

Different phases will in general comprise mutually differing formulation auxiliaries so that said phases can dissolve in the body at different times after oral administration.

However, in a dosage form it is in principle also possible for the phases forming the magnetic field to be produced with the same formulation auxiliaries provided that their location in the dosage form is selected such that the phases with in principle the same formulation nevertheless dissolve at different times in the body. This can be the case if, for example, one magnetic field forming phase is located in the outer region of the dosage form and another magnetic field forming phase is located on the inside, with it being possible for the phases possibly to be separated by a separating layer.

In the simplest case, the magnetizable particles together with powdery formulation auxiliaries and possibly a pharmaceutical agent can be pressed to form a tablet core. The core constitutes a magnetizable phase within the meaning of the invention. In general, the magnetizable particles will no longer be movable after pressing. The magnetization of the core phase can thus be effected by the magnetization of the elementary magnetic particles within the magnetizable particles as a result of a magnetic field acting from the outside. Thus the core can be converted into a phase forming a magnetic field.

Before magnetization, the core phase forming a magnetic field can also be provided with an encapsulation which likewise has magnetizable particles (encapsulation phase). The encapsulation can for example consist of a gastric juice resistant polymer. The encapsulated dosage form can then as a whole be subject to a magnetic field acting from the outside, as a result of which the core phase and the encapsulation phase are magnetized simultaneously. After intake into the body, the gastric juice resistant encapsulation as a first phase will quickly dissolve in the intestine, the magnetic field being lost in the process. The second phase, the core, can for example be formulated such that the dissolving is delayed and so the second magnetic field is only lost later. The superposition of the two magnetic fields and the successive loss thereof in the process of dissolving the dosage form yields a characteristic intensity profile over time.

Film-forming polymers can preferably be used as formulation auxiliaries for fixing the magnetizable particles. The magnetizable particles obtained can be magnetized by orienting them during the production in the nonsolid state, for example in the gel state or in the melt state. The magnetizable particles obtained can also be magnetized in the solid state by orienting the elementary magnets in the interior of the magnetizable particles.

Suitable formulation auxiliaries include, for example, copolymers of methyl methacrylate and ethyl acrylate, copolymers of methyl methacrylate and ethyl acrylate and methacrylic acid, copolymers of methyl methacrylate and methyl methacrylate and methacrylic acid and copolymers of methyl methacrylate, ethyl acrylate and trimethylammoniomethyl methacrylate. EUDRAGIT® E100, EUDRAGIT® E PO, EUDRAGIT® L100, EUDRAGIT® L100-55, EUDRAGIT® S, EUDRAGIT® FS, EUDRAGIT® RS or EUDRAGIT® RL, EUDRAGIT® NE or EUDRAGIT® NM are particularly suitable types of copolymers.

The following are also suitable: polyvinylpyrrolidone (PVP), polyvinyl alcohols, polyvinyl alcohol-polyethylene glycol-graft copolymer (Kollicoat®), starch and derivates thereof, polyvinyl acetate phthalate (PVAP, Coateric®), polyvinyl acetate (PVAc, Kollicoat), vinyl acetate-vinyl pyrrolidone copolymer (Kollidon® VA64), vinyl acetate:crotonic acid copolymers, polyethylene glycols with a molecular mass above 1000 (g/mol), chitosan, a (meth) acrylate copolymer, comprising 20-40% by weight of methyl methacrylate and 60 to 80% by weight of methacrylic acid, a crosslinked and/or uncrosslinked polyacrylic acid, a Na alginate, and/or a pectin, celluloses such as anionic carboxymethylcellulose and the salts thereof (CMC, Na-CMC, Ca-CMC, Blanose, Tylopur), carboxymethylethylcellulose (CMEC, Duodcell®), hydroxyethylcellulose (HEC, Klucel), hydroxypropylcellulose (HPC), hydroxypropylmethylcellulose (HPMC, Pharmacoat, Methocel, Sepifilm, Viscontran, Opadry), hydroxymethylethylcellulose (HEMC), ethylcellulose (EC, Ethocel®, Aquacoat®, Surelease®), methylcellulose (MC, Viscontran, Tylopur, Methocel), cellulose ester, cellulose glycolate, cellulose acetate phthalate (CAP, Cellulosi acetas PhEur, cellulose acetate phthalate, NF, Aquateric®), cellulose acetate succinate (CAS), cellulose acetate trimelliate (CAT), hydroxypropylmethylcellulose phthalate (HPMCP, HP50, HP55), hydroxypropylmethylcellulose acetate succinate (HPMCAS -LF, -MF, -HF) or a mixture of the mentioned polymers. Biodegradable polymers such as polylactic or polylactic co-glycolide, such as the various Resomer® products, are also suitable.

In addition to the film-forming polymers, further usual pharmaceutical auxiliaries which are not film-forming polymers can be used in a known manner as formulation auxiliaries or can additionally be contained. Here stabilizers, colorants, antioxidants, wetting agents, pigments, brighteners, flow aids, flavoring agents, fragrances, penetration promoting agents, plasticizers, pore-forming agents, glidants etc. should be mentioned by way of example. They are mainly used as processing auxiliaries and should ensure a reliable and reproducible production method and good long-term storage stability. Further usual pharmaceutical auxiliaries can be present in amounts of 0.001 to 30, preferably 0.1 to 10% by weight with respect to the film-forming polymer. For example, binding agents such as lactose, sucrose, glucose or starch are suitable as formulation auxiliaries.

The magnetically orientable or magnetizable particles can preferably be oriented with the aid of a magnetic field acting from the outside when the formulation auxiliary is in the nonsolid state. The orientation of the particles is fixed during the solidification of the formulation auxiliary and so magnetic field comprising phases are formed.

Biologically Active Agent

The dosage form according to the invention comprises at least one biologically active agent which can be located in one or more phases of the dosage form. A biologically active agent within the meaning of the invention is an agent which unfolds physiological or therapeutic action in the body after intake. Hence the term "biologically active agent" includes all nutritive (nutraceutical) and pharmaceutical agents. This is independent of whether this phase or these phases simultaneously also contains or contain magnetically oriented particles. The biologically active agent is preferably contained in the core of the dosage form or in an enclosed capsule. The invention is particularly suitable for monitoring the intake of critical medicines such as cardiovascular remedies where erroneous intake leads to the patient putting him/herself at risk.

Detection and Evaluation System

The strength of the magnetic fields in relation to the positions thereof in the body can be acquired using a detection system and can be evaluated using a computer-based evaluation system. The system serves the purpose of monitoring the intake of the dosage form according to the invention by a patient. In particular, the correct intake, inadvertent erroneous intake or other irregularities such as attempted manipulation of the system should be detectable.

The detection system can preferably be worn on the body and primarily comprises one or more, preferably two or three, sensors for measuring the magnetic fields. The sensors can preferably be based on the principle of the known Hall probe or the Hall sensor or a teslameter for measuring magnetic fields. A triangulating measurement by means of a plurality of sensors, namely two, three, four, five or more than five, sensors is preferred. The strength of the magnetic fields obtained in the dosage form, measured using a teslameter at a distance of 1 cm, can lie in the range of for example 1 to 1000, preferably 2 to 500, particularly preferably 5 to 250 µT. When measuring the magnetic fields in the human body, a distance of up to 100 cm, for example 1-30 cm, between the sensor and the source of the magnetic field in the dosage form can be assumed. Corresponding detection systems and sensors must still be able to detect the magnetic flux density which is reducing in intensity as a result of the distance. Hall probes or Hall sensors for measuring magnetic fields have sufficient sensitivity.

The detection system, for example one or more sensors, can for example be applied to the body directly on the skin or in the vicinity of the skin, but in any case at a distance which still suffices to ensure an error-free measurement of the magnetic fields within the body. In a particular embodiment, one or more parts of the detection system or the sensor setup can be attached under the skin or within the body using implant architecture known to a person skilled in the art. One or more sensors can be attached directly onto the skin, for example onto the abdominal wall and/or onto the neck. One or more sensors can be attached in the vicinity of the skin, for example directly in or on a piece of clothing.

The detection system and the computer-based evaluation system preferably comprise one or more sensors for detecting or measuring the magnetic field. The computer-based evaluation system preferably comprises a data processing part and a computer which is integrated into the data processing part or else can be present independently, and software for acquiring, calculating and evaluating the data.

The data processing part is used for storage or intermediate storage of the data and possibly also already for its evaluation or partial evaluation. A computer comprising all required processors, storage elements and peripheral parts which is equipped with corresponding software is integrated into the data processing part or else as a separate piece of equipment.

The required software can easily be created by a person skilled in the art in the field of information technology if the known or expected signal characteristics of the dosage form are known. In the process, the magnetic field signals can be measured in relation to the disturbance variables which emerge from the continual spatial change in position and alignment of the magnetic fields in the body with respect to the position of the sensor or sensors over time and said signals can be calculated taking into account the disturbance variables and the data can be related to each other. The data cleansed of the disturbance variables substantially correspond to the data which would be obtained in the case of a static measurement outside of the body. So as to create the software, a person skilled in the art can use for example techniques for modulating, recognizing modes, transformations, Fourier transformations etc., convolutions, correlations and autocorrelations, invariance determination, inter- and extrapolating error algorithms, line form analysis and removing disturbance fields. Auto-adaptive systems, such as neural networks and databases comprising expert systems, are preferably integrated.

The sensors and data processing part can be housed together in one instrument. Such an instrument is preferably designed such that it can easily be worn on the body. The size should not exceed approximately the following dimensions: 200×100×30 mm (length×breadth×height). The weight should be as low as possible and should not exceed approximately 500 g. The equipment can for example be attached to the abdominal wall of the patient using a carrying-strap system.

The sensors and data processing part are preferably present independently of one another. The sensors are preferably provided with a transmission-capable setup, which makes transmission of the data to the data processing part possible, which data processing part in turn can have interfaces for receiving data and for data transport. The sensors and the data processing part are preferably designed such that they are light, e.g. only 1 to 20 g for the sensors or 10 to 250 g for the data processing part, and can be attached to the body, e.g. on the neck, wrist, thorax or abdominal wall, and are hardly perceivable for the patient. The energy sources of the sensors and the data processing part are preferably self-sustaining or rechargeable. The sensors should particularly preferably enable wireless data transmission to the receiver part.

Use

The invention furthermore relates to the use of a dosage form according to the invention combined with a detection system and a computer-based evaluation system for the purpose of monitoring the intake of the dosage form by the patient. In terms of practice, the use can be integrated into numerous procedures. Erroneous intakes can thus be detected unambiguously and can be taken into account when evaluating studies or, in further progression, a therapy.

EXAMPLES

Example 1

Measuring the Magnetic Field Strength of Magnetically Orientable or Magnetizable Particles Embedded in Hydroxypropylmethylcellulose (HPMC)

360 g of distilled water were placed into a 500 ml laboratory bottle and heated to 70° C. whilst simultaneously stirring on a magnetic stirrer (IKA Combimag). 40 g of hydroxypropylmethylcellulose (METHOCEL® E5 Premium LV, Dow Chemicals) were added to the heated water and stirred for 10 minutes until the hydroxypropylmethylcellulose (HPMC) was completely dissolved. The temperature of the solution was then lowered to room temperature. 0.75 g of $Fe_3O_4$ powder with an average particle size in the region of approximately 20-200 µm (Sicovit® Black 80 E 172) was added to 39.25 g of the produced HPMC solution (10% m/m) in a Petri dish (VWR) with a diameter of 100 mm whilst simultaneously stirring on the magnetic stirrer for 10 minutes. The magnetic stirrer was stopped and the solution comprising the iron oxide ($Fe_3O_4$) was left to solidify on the magnetic stirrer at room temperature.

A further film with the same components was produced for comparison. However, said film was dried on a normal laboratory worktop at room temperature without a magnet being in the vicinity.

The measuring probe of a teslameter (model FM 220 from Projekt Elektronik GmbH) was attached to the bottom of an evaporating basin from the outside; the distance to the floor was 4 mm. The teslameter was now calibrated to 0 Tesla. The film magnetized on the magnetic stirrer was put into the evaporating basin, turned until the strongest magnetic field could be measured and subsequently fixed using object supports. Subsequently, distilled water heated to 37° C. was put into the evaporating basin. The magnetic field strength was then measured every second.
Result:
Initially, the signal could be measured to have a strength of 44 µT and its strength decreased down to 8 µT after the addition of water over a period of 300 seconds. It could be observed that the HPMC film was dissolved by the water and as a result the iron oxide particles aligned in the magnetic field were no longer in their aligned positions. The aligned magnetic field previously produced by the magnetic stirrer in the form of fixed iron oxide in HPMC is no longer present when the HPMC film dissolves. The comparison film showed no measureable magnetic field strength on the digital display of the teslameter (<1 µT).
FIG. 1: Magnetic field diagram for example 1. Measurement of the magnetic field strength of the magnetized film (in µ-Tesla) after adding heated demineralized water.

Example 2

Production of EUDRAGIT® Films Comprising Magnetite for Measuring the Magnetic Field Strength
99 g of distilled water were weighed out into a 250 ml laboratory bottle with 3 g of triethyl citrate (10% m/m based on TS polymer) and 100 g EUDRAGIT® L30 D-55 (EUDRAGIT® L100-55 is a copolymer of 50% by weight of ethyl acrylate and 50% by weight of methacrylic acid. EUDRAGIT® L 30D-55 is a dispersion comprising 30% by weight of EUDRAGIT® L 100-55). The components were stirred for 30 minutes at 400 rpm.
Subsequently, 750 mg of $Fe_3O_4$ (iron oxide, Sicovit® Black) were added to 19.25 g of the produced EUDRAGIT® L 30D-55 dispersion. The aqueous suspension was subsequently poured into a Petri dish coated in Teflon foil which was located on a magnetic stirrer. The magnetic field of the magnet contained in the magnetic stirrer then ensured an alignment of the fine-powdery iron oxide in the dispersion.
Result:
Over a period of 48 hours, the aqueous solution in the Petri dish formed a dry film in which the iron oxide was visibly aligned along the magnetic field lines of the magnet in the magnetic stirrer.

Example 3

Measuring the Change in Magnetic Field Strength as a Result of Temporally Different Dissolution of Two Magnetized Films in a Specific Spatial Arrangement in an Aqueous Medium
EUDRAGIT® E PO is a copolymer of 25% by weight of methyl methacrylate, 25% by weight of butyl methacrylate and 50% by weight of powdery dimethylaminoethyl methacrylate. EUDRAGIT® FS is a copolymer of 25% by weight of methyl methacrylate, 65% by weight of methyl acrylate and 10% by weight of methacrylic acid. EUDRAGIT® FS 30 D is a dispersion comprising 30% by weight of EUDRAGIT® FS.
0.75 g of iron oxide (($Fe_3O_4$) Sicovit® Black 80 E 172) was added to 19.25 g of neutralized EUDRAGIT® E PO solution (15% m/m in water) in a Petri dish coated in Teflon foil and mixed by stirring with the aid of a magnetic stirrer. After the stirring function was switched off, the film was left to dry on the magnetic stirrer at room temperature, with the iron oxide particles being aligned along the magnetic field.
0.75 g of iron oxide (($Fe_3O_4$) Sicovit® Black 80 E 172) was added to 19.25 g of EUDRAGIT® FS30 D dispersion in a Petri dish coated in Teflon foil and mixed by stirring with the aid of a magnetic stirrer. After the stirring function was switched off, the film was left to dry on the magnetic stirrer, with the iron oxide particles being visibly aligned along the magnetic field.
The sensor of the teslameter (see FIG. 2, 20) was attached to the underside of the bottom of the Petri dish (21) with a diameter of 14 cm. A plastic grid (22) was placed into the Petri dish, onto which the EUDRAGIT® E PO/iron oxide film (23) was placed. A EUDRAGIT® FS 30 D/iron oxide film (24) was affixed above the present film by means of clamps (25). In the process, the films were aligned such that the respective magnetic field strengths attained a maximum cancelation of the signal at the sensor at a distance of 1.1 cm. So as to prevent the films from floating during the trial, a plastic grid (22) was placed over the combination of films as termination of the examination system. 300 ml of distilled water (26) were firstly placed into the Petri dish. The magnetic field strength was measured every 60 seconds. The water was removed after 8 minutes. The pump system was used to place 300 ml of 0.1 N HCl solution (26) into the Petri dish until both films were completely covered. Thereafter, the HCl solution was circulated using the pump system. The magnetic field strength was measured every 60 seconds. The HCl solution was removed after 67 minutes. The pump system was now used to place 300 ml of 0.1 N NaOH solution (26) into the Petri dish until the remaining EUDRAGIT® FS/iron oxide film was completely covered. Thereafter, the NaOH solution was circulated using the pump system. The magnetic field strength was measured every 60 seconds. The trial was completed after 127 minutes.
Result:
The result is illustrated in the magnetic field diagram of FIG. 3.
During the time in which the films were in distilled water, no change could be observed in the structure of the films or in the strength of the magnetic field (min 0-8).
After adding the HCl solution, the EUDRAGIT® E PO/iron oxide film could be seen to dissolve. At the same time, a change in the magnetic field strength appeared: The field strength of the film combination, which initially was at −36 µT (micro-Tesla), was at +23 µT once the film (EUDRAGIT® E) had completely dissolved (min 9-67).
After adding NaOH, the other film (EUDRAGIT® FS 30) could be seen to dissolve and there was a change in the magnetic field strength from +24 µT to 8 µT after 127 minutes (min 68-127).

Example 4

Production of HPMC Capsules, Comprising a EUDRAGIT® E Film with a Fixed $Fe_3O_4$ Powder which is Aligned with the Magnetic Field
1.5 g of a EUDRAGIT® E PO solution (15% m/m) was provided in a glass bottle. 3 g of iron oxide powder ($Fe_3O_4$) and 1.5 g of polyethylene glycol ((PEG) Macrogol® 300) were added and admixed with a plastic rod by stirring until a homogeneous mass resulted. The resultant paste was put into a syringe.
Using the syringe, so much paste (FIG. 4, 40) was pressed into the lower part of a size 0 hard gelatin capsule (41) until the rounded part of the bottom of the capsule was covered with the paste (40). The lower part of a size 1 capsule (42) was now pressed into the filled capsule and rotated (movement vectors 43), and so the filled in paste (40) was distributed over the bottom and over the gap created between the wall of the size 0 capsule and the size 1 capsule. Subsequently, the capsule half prepared in this fashion was placed at room temperature (approximately 23° C.) with the opening on a permanent magnet (44, round, (14×5 mm)) for 12 hours and stored there until the material was completely dry. Using a teslameter, the capsule half coated in this fashion and treated by the magnet was measured at a distance of 1 cm. A magnetic field with a strength 30 µT was determined.

Result:

The paste comprising the iron oxide was securely and durably bound to the inner wall of the hard gelatin capsule half after the treatment. The capsule half produced in this fashion is provided with a measurable magnetic field and can be used as a phase of a dosage form which forms a magnetic field.

Example 5

Production of Combined Capsules (Gelatin and HPMC) with Magnetic Components with Differently Aligned Magnetic Field A size 0 lower capsule half was produced in accordance with the method in example 4. A size 4 lower capsule half was produced in a fashion analogous to example 4. In this example, the magnetic field strength of the smaller capsule half was measured to be 160 µT at a distance of 1 cm and the larger capsule half had a magnetic field strength of 180 µT. The size 4 lower capsule half was closed off using a size 4 upper capsule half. 200 mg of maltitol (a hydrogenated disaccharide (Maltisorb®)) were now filled into the size 0 capsule half to ensure that the small capsule (size 4) was fixed in the large capsule (size 0). The inner capsule (size 4) was now fixed or rotated in the outer capsule (size 0) such that the two superposing magnetic fields resulted in the lowest possible field strength. This resulted in a resultant magnetic field strength of 40 µT at a distance of 1 cm. The size 0 lower capsule half was closed off using a size 0 upper capsule half.

The "capsule in the capsule" produced in this exemplary manner constitutes a dosage form according to the invention with the proviso that it still contains no agent. However, it is obvious to a person skilled in the art that an agent can optionally or in a combined form be inserted between the capsules or in the interior space of the smaller capsule.

Example 6

Production of Tablets with Magnetic Layers and Components as a Phase for a Dosage Form A drop of paraffin wax was in each case placed in a PE blister packaging film with twelve 8 mm (diameter) recesses. Subsequently, 5 drops of a neutralizing EUDRAGIT® E PO solution (15% m/m, pH 7.0) were added into the indentation of the PE blister pack and thereafter it was placed into a drying cabinet at 40° C. and dried. Once a dried EUDRAGIT® E PO film had formed, 50 mg of iron oxide powder were added into the indentation in the PE blister packaging film. Subsequently, 5 further drops of the neutralizing EUDRAGIT® E PO solution were added and the PE blister packaging film was placed onto a round permanent magnet (14×5 mm) for aligning the iron oxide particles. The blister pack (together with the magnet) was thereafter again dried at 40° C. in the drying cabinet.

200 mg of a placebo tablet mixture were put into the lower stamp (12 mm) of an eccentric tablet press ERWEKA type EP-1. The dried EUDRAGIT® E PO core with the iron oxide from the PE blister packaging film was placed onto the tablet mixture. Subsequently, the lower stamp was filled to the upper edge with additional placebo tablet mixture. The mixture was subsequently pressed into tablet form using a pressure of between 8 and 15 kN.

Result:

This produced tablets which had a magnetic field that could be measured using a teslameter. So as to obtain a dosage form according to the invention, an agent and a second phase forming a magnetic field would have to be added, the dissolving properties of which differ from the phase in the tablet interior.

The invention claimed is:

1. An oral dosage form, comprising a biologically active agent, a formulation auxiliary substance and magnetizable particles, wherein the dosage form has a composition of at least two phases, wherein the phases can dissolve in a body after oral administration and wherein the magnetizable particles are bound in the formulation auxiliary substance and are present in a magnetized state,
wherein
the magnetizable particles are present in at least two phases of the dosage form and generate magnetic fields, wherein at least two of the magnetic fields have different alignments, wherein the phases dissolve at different times in the body after oral administration, and wherein a magnetic field strength with respect to time, position and movement in the body can be acquired using a detection system and can be evaluated using a computer-based evaluation system.

2. The dosage form of claim 1, wherein the magnetic fields yield a characteristic intensity spectrum over time that can be acquired using the detection system and the evaluation system.

3. The dosage form of claim 1, wherein the dosage form has a composition of at least three phases, wherein the magnetizable particles are present in three phases of the dosage form.

4. The dosage form of claim 1, wherein the dosage form has a composition of at least three phases, wherein at least one phase comprises the biologically active agent but no magnetizable particles.

5. The dosage form of claim 1, wherein at least one phase comprising magnetizable particles is an immediate release phase.

6. The dosage form of claim 1, wherein the magnetic field strength, measured using a teslameter at a distance of 1 cm, is 1 to 1000 µT.

7. The dosage form of claim 1, wherein the magnetic fields are localized to at least one part of the dosage form selected from the group consisting of a core, a polymer film encapsulation, and a capsule half.

8. The dosage form of claim 1, wherein the magnetizable particles comprise magnetite ($Fe_3O_4$) or maghemite ($Fe_2O_3$).

9. The dosage form of claim 1, wherein the dosage form is a filled capsule, a filled capsule which is enclosed in a further capsule, or an encapsulated tablet.

10. A method for producing the dosage form of claim 1, comprising
binding, in two or more phases, the magnetizable particles to the formulation auxiliary substance,
magnetizing the magnetizable particles by an external magnetic field, and
joining the phases to obtain a dosage form,
wherein the magnetizing can be performed before or after the joining phase.

11. The method of claim 10, wherein the binding and magnetizing are performed when the formulation auxiliary substance is in a nonsolid state, and the formula auxiliary substance subsequently transitions from the nonsolid state to a solid state, to obtain oriented magnetizable particles.

12. The method in of claim 10, wherein the magnetizing is performed before the joining, and the joining optionally comprises an additional phase.

13. The method of claim 10, wherein the formulation auxiliary substance is a film-forming polymer.

14. The method claim 11, wherein the nonsolid state is a gel state or a melt state.

15. The method of claim 12, wherein the one or more phases are two magnetized films having oppositely directed magnetic fields, and the joining is a joining of the two magnetized films to two opposite sides of a flat tablet core comprising the biologically active agent.

16. The method of claim 10, wherein the dosage form further comprises a capsule half.

17. The method of claim 16, wherein the binding is dip-coating the capsule half in a mixture comprising a film-forming polymer, a solvent and magnetizable particles to obtain a coating on a capsule half, the magnetizing is performed when the coating is in a nonsolid state, and the coating subsequently transitions from the nonsolid state to a solid state.

18. The method of claim 10, wherein one or more phases comprise a magnetized, extruded core.

19. The method of claim 18, wherein the binding is strand extruding the extruded core from a preparation comprising a film-forming thermoplastic polymer, optionally an agent and magnetizable particles, and subsequently comminuting the extruded core into an elongate or a planar phase, and the magnetizing is performed when the extruded core is in a melt state, and the extruded core subsequently cools to obtain oriented magnetizable particles.

20. A method of monitoring an intake of the dosage form of claim 1, the method comprising administering the dosage form to a patient, detecting a magnetic field strength with a detection system, and evaluating with a computer-based evaluation system.

* * * * *